_United States Patent_ [19]

Bruns

[11] Patent Number: 4,705,758
[45] Date of Patent: Nov. 10, 1987

[54] ADENOSINE RECEPTOR ASSAY AND KIT

[75] Inventor: Robert F. Bruns, Ann Arbor, Mich.

[73] Assignee: Warner-Lambert Company, Morris Plains, N.J.

[21] Appl. No.: 622,353

[22] Filed: Jun. 19, 1984

[51] Int. Cl.⁴ .................. G01N 33/567; G01N 33/534
[52] U.S. Cl. .................................... 436/504; 436/503; 436/545; 436/804; 436/817
[58] Field of Search ............... 436/501, 504, 503, 545, 436/804, 817

[56] References Cited

U.S. PATENT DOCUMENTS 4,431,742  2/1984  Rosenblatt .......................... 436/504
4,528,131  7/1985  Kardos et al. ...................... 436/504

FOREIGN PATENT DOCUMENTS 2902071  7/1979  Fed. Rep. of Germany ...... 436/504

OTHER PUBLICATIONS

Church et al., Br. J. Pharmac., 80, (1983), 719–726.
Goodman et al., Chem. Abstract, 98, (1983), #47469y.
Bruns et al., Proc. Natl. Acad. Sci. USA, 77, (1980), 5547–5551.

_Primary Examiner_—Christine M. Nucker
_Attorney, Agent, or Firm_—Ronald A. Daignault

[57] ABSTRACT

Certain substituted adenosines have been found to selectively occupy $A_1$ adenosine receptors found in animal brain tissues.

12 Claims, 1 Drawing Figure

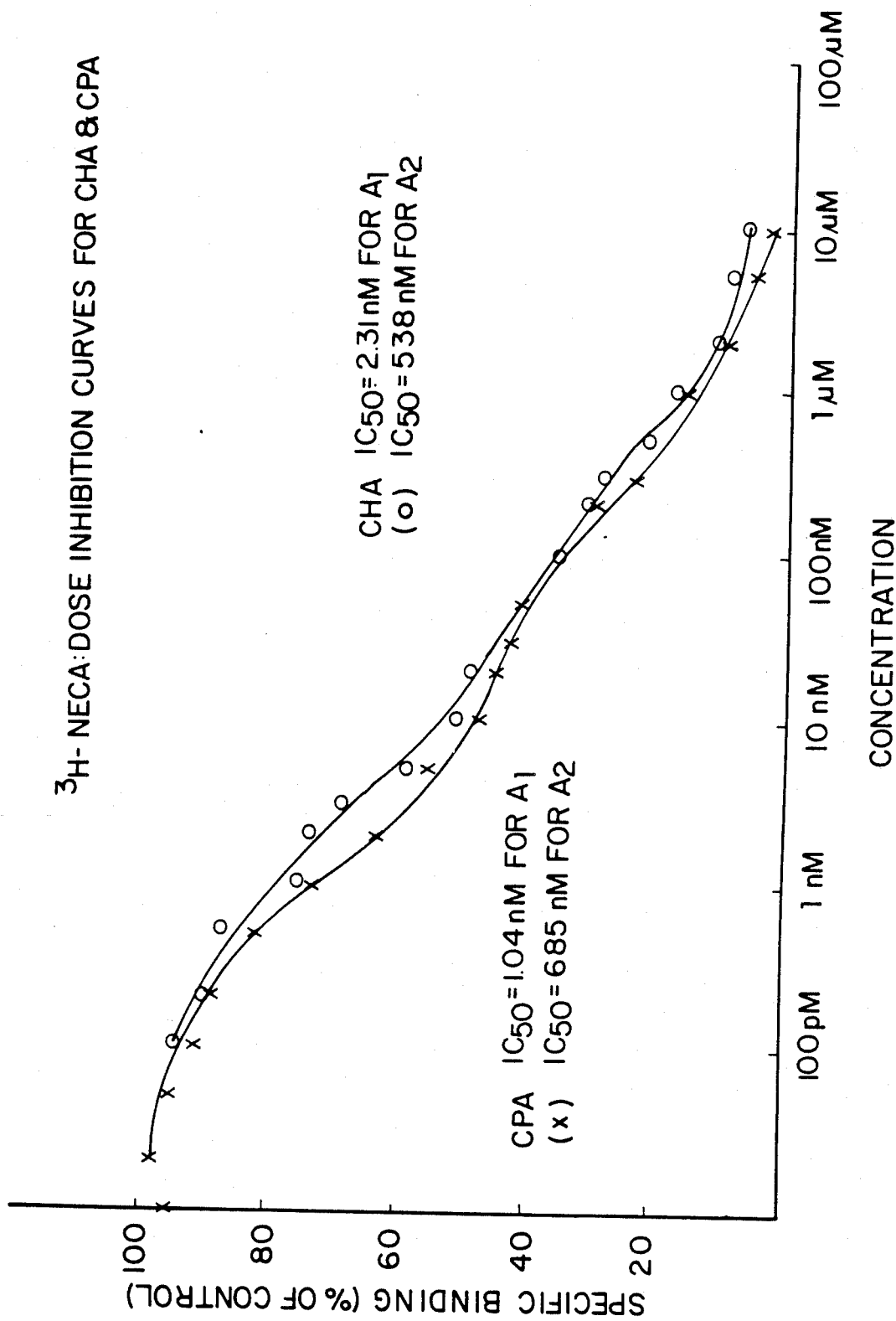

ADENOSINE RECEPTOR ASSAY AND KIT

BACKGROUND

Adenosine is known to affect adenylate cyclase activity in various parts of the body. Since adenosine receptors can be characterized as $A_1$ receptors (which inhibit adenylate cyclase) and $A_2$ receptors (which increase adenylate cyclase activity), the need arose for a screening technique which could measure affinities of various drugs for these receptors.

Since selectivity for $A_2$ adenosine receptors is characteristic of certain neuroloptic drugs, the isolation of $A_2$ receptors is an important step in the screening of drugs, particularly neuroleptic and antipsychotic drugs. Tritiated 5'-N-ethyl carboxamide adenosine, [$^3$H]NECA, is a labelled ligand which is known to stimulate adenylate cyclase and, as such, has a high affinity for adenosine receptors. However [$^3$H]NECA will interact with both $A_1$ and $A_2$ receptors. Accordingly, it became desirable to find a method and reagent via the use of which $A_2$ receptors could be assayed without significant interference from the presence of $A_1$ receptors. Researcher Siu-Mei Helena Yeung and Richard D. Green have investigated the binding of $N^6$-cyclohexyl adenosine (CHA) in rat brain striatum containing labelled 5'-N-ethyl carboxamide adenosine. Their work was published in *Naunyn-Schmiedeberg's Arch. Pharmacol.*, 325:218–225 (1984).

THE INVENTION

It has been discovered that the affinity of compounds for $A_2$ adenosine receptors can be tested by using, prior to or concomitant with the testing, a displacer or selective occupier which functions to occupy any $A_1$ receptors in the medium while leaving $A_2$ receptors available for reaction. One specific embodiment of the invention involves a test kit containing lyophilized rat striatal brain membrane, [$^3$H]NECA containing liquid, and a suitable quantity of one or more displacers selected from $N^6$-cyclopentyl adenosine (CPA) and $N^6$-(3-hydroxypropyl) adenosine (HPA). It was found that these displacers, when added in proper amounts, exhibit the capacity to occupy an insignificant percentage of the total number of $A_2$ receptors while occupying virtually all of the $A_1$ receptors. Following the use of the displacer, the unoccupied receptor molecules, principally $A_2$ receptor molecules, can be employed in testing via appropriate reaction(s), to screen or otherwise test drugs for psychological effects.

DESCRIPTION OF THE INVENTION

The invention deals with the selective binding of certain compounds to $A_1$ receptors. Due to the unique affinity of these compounds for $A_1$ receptors, there is selective binding to $A_1$ receptors. This binding results in the displacement or occupation of $A_1$ receptors with little, or virtually no, occupation of $A_2$ receptors. By using one or more of these displacers in combination with a labelled compound which has an affinity for both $A_1$ and $A_2$ receptors a competitive assay system results. In such a combination, it is preferred that the displacer(s) be unlabelled.

Thus, the invention provides a method of occupying significant amounts of $A_1$ adenosine receptors with insignificant occupation of $A_2$ receptors in a material containing both. Furthermore, it provides a competitive assay technique in which a labelled reagent which has an affinity for, or binds, both $A_1$ and $A_2$ receptors competes with the $A_1$ selective reagent for binding to significant proportions of $A_1$ receptors.

Typically the displacer(s) will be employed in a scheme which includes the step of contacting a preparation—i.e., a solution, suspension or solid combination—containing both $A_1$ and $A_2$ receptors with a material, i.e., a solution or solutions, containing at least one labelled ligand which has a high affinity for both $A_1$ and $A_2$ receptors in the presence of an unlabelled displacer which selectively occupies $A_1$ receptors with insignificant, i.e., negligible or no, occupation of $A_2$ receptors.

In other words, the invention rests on the discovery that the binding activity of $A_1$ receptors, in a material containing $A_1$ and $A_2$ receptors, can be effectively eliminated by contacting that material with a suitable quantity of an unlabelled displacer for a period of time sufficient for the occupation of a majority, or substantially all, of the $A_1$ receptors by the displacer.

Furthermore, the fact that these displacers usually act independently of any other ligand present renders them suitable as components of an assay kit for adenosine receptors. Thus the subject displacer(s), with or without labelled binding reagent(s) and suitable animal tissue can be used in a test kit for assaying adenosine receptors.

THE DISPLACER

The displacers or selective occupiers of this invention are characterized by their high affinity to $A_1$ adenosine receptors and their low or insignificant affinity to $A_2$ receptors. Their affinity for $A_1$ receptors is so great that they displace other well-known solutes which are bound to, or compete for binding to, $A_1$ sites.

While some limited binding or occupation at $A_2$ sites occur, that binding is minimal. As the discussions of the drawing will show, the affinity of the subject displacers to $A_2$ receptors is so small that it would require very large amounts of the displacer(s) to "force" reaction with $A_2$ receptors. Even if forced reactions were effected, the selective occupiers would have, in effect, exhausted all $A_1$ receptors in the system before beginning to bind to $A_2$ receptors.

The selective displacers of this invention are adenosine derivatives having the requisite selective affinity for $A_1$ receptors in animal brain tissues. When used at proper concentrations, substituted adenosines, preferably $N^6$-alkyl- or $N^6$-hydroxyalkyl-adenosine in which the alkyl moietries contain from about 3 to about 8 carbon atoms exhibit this property. Preferred displacers include cycloalkyl adenosines, e.g., $N^6$-cyclooctyladenosine, $N^6$-cycloheptyl adenosine, and $N^6$cyclopentyl adenosine (CPA); and hydroxyl substituted adenosines, e.g., $N^6$-(3-hydroxypropyl)-adenosine (HPA), and the like. While mixtures of substituted adenosines are operable, it is generally preferred that suitable quantities of only one can be used in one binding and/or assay procedure. Although CPA is known to the chemical literature, there is little or no public information on its interactions with adenosine receptors.

The quality of displacer to be employed depends upon such factors as the quantity and type of tissue being tested, and the nature of the labelled liquid, if any, being employed. Generally, the amount of displacer used will lie between about 20 nM (nanomolar) and about 500 nM, preferably about 100 nM, and will depend upon the relative $A_1$ and $A_2$ affinities of the displacer. For CPA, suitable quantities are from about 20 nM to about 100 nM, with about 50 nM preferred. For HPA, suitable quantities are from about 100 nM to about 500 nM, with about 250 nM preferred. Concentrations are calculated based upon the volume of the final incubation compositions.

LABELLED LIGAND

The assay techniques of the invention generally calls for the presence of a labelled competitor solute or reagent in the system. The ligand selected will depend upon the method to be used to quantify its presence in the system.

If a radio-based assay is desired, a suitable radiolabelled liquid, for example, tritiated 5'-N-ethyl-carboxamide adenosine, [$^3$H], can be employed. Other suitable radio-ligands include tritiated 5'-N-cyclopropylcarboxamide adenosine and the like. While mixtures are operable, it is generally preferred that only one radio-labelled ligand be used in each assay procedure.

If colorimetric and/or other quantifying techniques are employed, suitable reagents must e selected for their affinities for one or both of the $A_1$ and $A_2$ receptors as well as for their compatability and effectiveness in the presence of the displacers described above.

Suitable quantities of labelled solutes will lie between about 0.1 nM and about 10 nM, based on affinity and specific activity, with amounts of about 1 nM to about 5 nM preferred.

TISSUES TO BE TESTED

While the separation and assay techniques of the invention are especially useful for distinguishing compounds which have some affinity for adenosine receptors from those which have no or negligible affinity in brain tissue, and, preferably, rat striatal brain tissue, they can also be employed in other animal tissues in which $A_1/A_2$ receptor binding takes place, such as blood platelets and placenta.

When brain tissue is used, it must be suitably treated, e.g., homogenized, centrifuged several times to remove soluble components, stored frozen at $-70°$ C., or lyophilized, prior to the use of the reagents discussed.

Using well-known incubation techniques, the incubation of the tissue sample with one or more of the subject reagents will last from about 30 minutes to about 240 minutes. Preferably, incubation takes about 60 minutes.

The final mixture, after incubation, can be tested as is or may be subjected to suitable incubation termination and/or other techniques which assist in the recovery of the labelled or unlabelled substance to be quantified. Suitable techniques include filtration, centrifugation, dialysis, and the like.

While it is generally preferred that only the competing solute, e.g., NECA, be labelled, the invention is also operable if the displacer ligand is labelled, e.g., with a suitable radio tag.

The following examples and the drawing further illustrate the invention.

EXAMPLE

Materials. [$^3$H]NECA (N-ethyl-5'-carboxamide adenosine) was from Amersham (specific activity 27 Ci/mmol) or New England Nuclear (specific activity 30 Ci/mmol). [$^3$H]NECA from both sources gave essentially the same results. Adenosine deaminase was Sigma Type III, Tris.HCl (Tris) was sigma pH 7.7 pre-set crystals, GF/B filters were from Whatman, Formula 947 was from New England Nuclear, and N$^6$-cyclopentyladenosine was synthesized by Dr. Walter Moos at Warner-Lambert Co., Parke-Davis Division.

"Tris.HCl" and "Tris" refer to tris-(hydroxymethyl) aninomethane (made by Sigma Chemical Co.).

Tissue Preparation. Brains from 200–500 g mixed sex Sprague-Dawley rats were purchased from Pel-Freez (Rogers, Ark.). Fresh brains from male Long-Evans hooded rats (Blue Spruce Farms, Altamont, N.Y.) gave essentially identical results. Brains were thawed and then kept on ice while the striata were dissected out. Striata were disrupted in 10 vol of ice-cold 50 nM Tris.HCl (pH 7.7 at 25° C., pH 8.26 at 5° C.) (Tris) for 30 seconds in a Polytron PT-10 (Brinkman) at setting 5. The suspension was centrifuged at 50,000×g for ten minutes, the supernatant discarded, the pellet resuspended in 10 vol ice-cold Tris as above, recentrifuged, resuspended at 1 g/5 ml, and stored in plastic vials at $-70°$ C. (stale for at least six months). When needed, tissue was thawed at room temperature, disrupted in a Polytron, and kept on ice until used.

Incubation Conditions. All incubations were in triplicate for 60 minutes at 25° C. in 12×75 mm glass tubes containing 1 ml Tris with 5 mg original tissue weight of rat striatal membranes, 4 nM[$^3$H]NECA, 50 nM N$^6$cyclopentyladenosine (to eliminate $A_1$ receptor binding), 10 nM MgCl$_2$, 0.1 units/ml of adenosine deaminase (calculated from manufacturer's specifications), and 1% dimethylsulfoxide.

N$^6$-Cyclopentyladenosine was dissolved at 10 mM in 0.02N HCl and diluted in Tris. Stock solutions and dilutions of n$^6$-cyclopentyladenosine could be stored at $-20°$ C. for several months. Test compounds were dissolved at 10 mM in dimethylsulfoxide on the same day as the experiment, and diluted in dimethysulfoxide to 100x the final incubation concentration. Control incubations received an equal volume (10 μl) of dimethylsulfoxide; the resulting concentration of dimethylsulfoxide had no effect on binding.

[$^3$H]NECA was diluted to 40 nM in Tris. The membrane suspension (5 mg/0.79 ml) contained sufficient MgCl$_2$ and adenosine deaminase to give 10 mM and 0.1 units/ml, respectively, final concentration in the incubation. For test compounds with IC$_{50}$* values less than 1 μM, the order of addition was test compound (10 μl), N$^6$-cyclopentyladenosine (100 ul), [$^3$H]NECA 100 ul), and membranes (0.79 ml).

For test compounds with IC$_{50}$% values greater than 1 μM and limited water solubility, the order of addition (same volumes) was test compound, membranes N$^6$-cyclopentyladenosine, and [$^3$H]NECA. After all additions, the rack of tubes was vortexed, and the tubes were then incubated for 60 minutes at 25° C. in a shaking water bath. The rack of tubes was vortexed an additional time halfway through the incubation.

Incubations were terminated by filtration through 2.4 cm GF/B filters under reduced pressure. Each tube was filtered as follows: the contents of the tube were poured onto the filter, 4 ml of ice-cold Tris was added to the tube and the contents poured onto the filter and the filter was washed twice with 4 ml of ice-cold Tris.

The filtration was complete in about twelve seconds. A Brandel 24R or 48R cell harvester may also be used for the filtration.

Filters were put in scintillation vials, 8 ml of Formula 947** scintillation fluid added, and the vials left overnight, shaken, and counted in a liquid scintillation counter at 40% efficiency.

**"Formula 947" refers to a brand of scintillation fluid (made by New England Nuclear).

The scintillation counter employed was an LS6800 or LS9800, manufactured by Beckman Instruments. Other functionally equivalent devices are operable.

Data Analysis. Nonspecific binding was defined as binding in the presence of 100 μM $N^6$cyclopentyladenosine, and specific binding was defined as total binding minus nonspecific binding. The $IC_{50}$* was calculated by weighted nonlinear least squares curve-fitting to the mass-action equation:

$$Y = T - S \cdot \frac{D}{D + K}$$

where
Y is cpm bound
T is cpm total binding without drug
S is cpm specific binding without drug
D is the concentration of drug
and K is the $IC_{50}$ of the drug.

Weighted factors were calculated under the assumption that the standard deviation was proportional to the predicted value of Y. Nonspecific binding was treated as a very large (infinite) concentration of drug in the computer analysis.

*$IC_{50}$ can be defined at the concentration at which the test compound inhibits the binding of, or displaces 50% of, the competitor ligand, here [$^3$H]NECA.

THE DRAWING

The drawing is a graph representing the $^3$H-NECA Dose Inhibition Curves for CHA and CPA. The curves show the effects of different concentrations of CHA and CPA on total binding of $^3$H-NECA to rat striatal membranes. Experimental procedures were exactly as described in the Example, except that the addition of 50 nM CPA to each tube was omitted.

As the drawing indicates, CPA is a particularly effective displacer. When compared to CHA ($N^6$-cyclohexyl adenosine), its dose inhibition curve "flattens out" better (i.e., better approximates the theoretical ideal of a flat central region in the curve). The existence of a flat central region in the curve allows the selection of a concentration of displacer (in this case CPA) which will occupy substantially all of the $A_1$ of the $A_2$ sites.

Reasonable variations, such as those which would occur to a skilled artisan, can be made herein without departing from the scope of the invention.

I claim:

1. A method for measuring affinities of compounds of adenosine $A_2$ receptors without significant interference from adenosine $A_1$ receptors comprising: contacting a preparation (solution, suspension, or solid) containing both $A_1$ and $A_2$ receptors with a solution or solutions containing at least one labelled ligant which has high affinity for both $A_1$ and $A_2$ receptors and a suitable quantity of an unlabelled displacer which selectively occupies $A_1$ receptors without significant occupation of $A_2$ receptors, wherein the displacer contains at least one compound selected from the group consisting of: $N^6$(3-hydroxypropyl)adenosine, and $N^6$-cycloalkyl adenosines in which the alkyl moiety contains 5, 7 or 8 carbon atoms; and measuring the amount of labelled ligand as an indication of affinity to the $A_2$ receptors.

2. The method of claim 1 wherein the displacer contains $N^6$-cyclopentyladenosine or $N^6$-(3-hydroxypropyl) adenosine.

3. The method of claim 1 wherein the labelled ligand is tritiated 5'-N-ethyl carboxyamide adenosine.

4. The method of claim 2 wherein the labelled ligand is tritiated 5'-N-ethyl carboxyamide adenosine.

5. A method for eliminating $A_1$ receptor binding activity from materials containing $A_1$ and $A_2$ receptors comprising the step of contacting the material with a suitable quantity of an unlabelled displacer until a majority of the $A_1$ receptors are occupied by the displacer, wherein the displacer is selected from the group consisting of: $N^6$(3-hydroxypropyl) adenosine, and $N^6$-cycloalkyl adenosines in which the alkyl moiety contains 5, 7 or 8 carbon atoms and mixtures thereof, the amount of unlabelled displacer being sufficient to eliminate $A_1$ receptor binding activity.

6. The method of claim 5 wherein the displacer is $N^6$-cycloalkyladenosine and it is present at a concentration of about 20 nM to about 100 nM, based on the volume of the final incubation composition.

7. The method of claim 5 wherein the displacer is $N^6$-(3-hydroxypropyl) adenosine and it is present in a concentration of about 100 nM to about 500 nM, based on the volume of the final incubation composition.

8. A test kit for assaying adenosine receptors in order to distinguish $A_1$ from $A_2$ receptors which kit comprises in separate containers a reagent containing a suitable quantity of unlabelled displacer which selectively occupies $A_1$ receptors without significant occupation of $A_2$ receptors; and suitable quantities of lyophilized animal tissue and labelled ligant, wherein the displacer is selected from the group consisting of: $N^6$(3-hydroxypropyl)adenosine, and $N^6$-cycloalkyl adenosines in which the alkyl moiety contains 5, 7 or 8 carbon atoms and mixtures thereof.

9. The kit of claim 8 wherein the animal tissue contains rat brain membrane.

10. The kit of claim 9 wherein the labelled ligand is tritiated 5'-ethyl carboxamide adenosine.

11. The kit of claim 10 wherein the displacer is $N^6$-cyclopentyladenosine.

12. The kit of claim 10 wherein the displacer is $N^6$(3-hydroxypropyl) adenosine.

* * * * *

UNITED STATES PATENT AND TRADEMARK OFFICE
CERTIFICATE OF CORRECTION

PATENT NO. : 4,705,758
DATED : November 10, 1987
INVENTOR(S) : Robert F. Bruns

It is certified that error appears in the above-identified patent and that said Letters Patent is hereby corrected as shown below:

Column 1, line 54, "ligant" should read -- ligand --.

Column 6, line 42, "ligant" should read -- ligand --.

Signed and Sealed this

Fifteenth Day of March, 1988

Attest:

*Attesting Officer*

DONALD J. QUIGG

*Commissioner of Patents and Trademarks*